United States Patent
Arhancet et al.

(10) Patent No.: US 9,801,845 B2
(45) Date of Patent: Oct. 31, 2017

(54) ANTIMICROBIAL COMPOSITIONS AND USES THEREOF

(71) Applicant: Novus International Inc., St. Charles, MO (US)

(72) Inventors: Graciela B. Arhancet, St. Charles, MO (US); Matthew Mahoney, St. Charles, MO (US); Scott Long, St. Charles, MO (US); Mariya Grega, St. Charles, MO (US); Drew L. Lichtenstein, St. Charles, MO (US); Vivek Kuttappan, St. Charles, MO (US); Jeffery Escobar Monestel, St. Charles, MO (US); Mercedes Vazquez-Anon, St. Charles, MO (US)

(73) Assignee: Novus International, Inc., St. Charles, MO (US)

( * ) Notice: Subject to any disclaimer, the term of this patent is extended or adjusted under 35 U.S.C. 154(b) by 0 days.

(21) Appl. No.: 15/196,420

(22) Filed: Jun. 29, 2016

(65) Prior Publication Data

US 2017/0000755 A1    Jan. 5, 2017

Related U.S. Application Data

(60) Provisional application No. 62/187,864, filed on Jul. 2, 2015.

(51) Int. Cl.

| A61K 31/795 | (2006.01) |
| --- | --- |
| A61K 31/23 | (2006.01) |
| A61K 31/225 | (2006.01) |
| A23K 20/105 | (2016.01) |
| A01N 41/00 | (2006.01) |
| A01N 55/00 | (2006.01) |
| A23K 10/18 | (2016.01) |
| A23K 20/174 | (2016.01) |
| A23K 20/111 | (2016.01) |
| A23K 20/142 | (2016.01) |
| A23K 20/158 | (2016.01) |
| A23K 20/163 | (2016.01) |
| A23K 20/10 | (2016.01) |
| A23K 20/189 | (2016.01) |
| A23K 20/195 | (2016.01) |
| A23K 20/28 | (2016.01) |
| A23K 20/20 | (2016.01) |
| A23K 50/10 | (2016.01) |
| A23K 50/75 | (2016.01) |
| A23K 50/30 | (2016.01) |
| A23K 50/40 | (2016.01) |
| A23K 50/80 | (2016.01) |
| A23K 30/00 | (2016.01) |
| A61K 45/06 | (2006.01) |
| A61K 31/80 | (2006.01) |

(52) U.S. Cl.
CPC .............. *A61K 31/23* (2013.01); *A01N 41/00* (2013.01); *A01N 55/00* (2013.01); *A23K 10/18* (2016.05); *A23K 20/10* (2016.05); *A23K 20/105* (2016.05); *A23K 20/111* (2016.05); *A23K 20/142* (2016.05); *A23K 20/158* (2016.05); *A23K 20/163* (2016.05); *A23K 20/174* (2016.05); *A23K 20/189* (2016.05); *A23K 20/195* (2016.05); *A23K 20/28* (2016.05); *A23K 20/30* (2016.05); *A23K 30/00* (2016.05); *A23K 50/10* (2016.05); *A23K 50/30* (2016.05); *A23K 50/40* (2016.05); *A23K 50/75* (2016.05); *A23K 50/80* (2016.05); *A61K 31/225* (2013.01); *A61K 31/795* (2013.01); *A61K 31/80* (2013.01); *A61K 45/06* (2013.01)

(58) Field of Classification Search
None
See application file for complete search history.

(56) References Cited

U.S. PATENT DOCUMENTS

| 6,949,498 | B2 | 9/2005 | Murphy | |
| --- | --- | --- | --- | --- |
| 2004/0175434 | A1 | 9/2004 | Schasteen | |
| 2006/0105960 | A1* | 5/2006 | Erdelmeir | ................ A61K 8/58 514/21.9 |
| 2013/0178540 | A1 | 7/2013 | Grady | |
| 2013/0209392 | A1 | 8/2013 | Arhancet | |

FOREIGN PATENT DOCUMENTS

| EP | 0572271 A2 | 12/1993 |
| --- | --- | --- |
| EP | 2082739 A1 | 7/2009 |
| WO | 2013150058 A1 | 10/2013 |
| WO | 2017004161 A1 | 1/2017 |

OTHER PUBLICATIONS

International Search Report and Written Opinion dated Sep. 19, 2016 from related international Application No. PCT/US16/40025, 8 pgs.
Annett et al.,. 2002. Necrotic enteritis: effect of barley, wheat and corn diets on proliferation of Clostridium perfringens type A. Avian Pathology, 2002, 31: 599-602.
Lensing et al., Efficacy of a lactylate on production performance and intestinal health of broilers during subclinical Clostridium Perfringens infection, Poultry Science, 2010, 89:2401-2409.

* cited by examiner

*Primary Examiner* — Deepak Rao
*Assistant Examiner* — Laura Daniel
(74) *Attorney, Agent, or Firm* — Polsinelli PC (57) ABSTRACT

Antimicrobial compositions comprising sulfur- or selenium-containing, fatty-acylated alpha-hydroxy acid compounds and methods of using said compounds or compositions to inhibit microbial growth.

22 Claims, 2 Drawing Sheets

ANTIMICROBIAL COMPOSITIONS AND USES THEREOF

CROSS-REFERENCE TO RELATED APPLICATIONS

This application claims the priority of U.S. provisional Application No. 62/187,864, filed Jul. 2, 2015, which is hereby incorporated by reference in its entirety.

FIELD

The present disclosure generally relates to antimicrobial compositions and methods for inhibiting microbial growth.

BACKGROUND

Antimicrobial resistance is a global public health concern. Since the 1940s, antimicrobial drugs have greatly reduced illness and death from infectious diseases. However, these drugs have been used so widely and for so long that some infectious organisms have developed resistance to the antimicrobial drugs that were originally effective in treating infections caused by them. Some microorganisms have even become resistant to multiple types or classes of antimicrobial drugs. Thus, there is an urgent need for the development of new antimicrobial agents and compositions.

SUMMARY

Among the various aspects of the present disclosure is the provision of an antimicrobial composition comprising at least one compound of Formula (I) and at least one agent chose from an essential oil, a metal chelate, a mineral, an amino acid, an organic acid, a vitamin, an antioxidant, a polyunsaturated fatty acid, a prebiotic, a probiotic, a symbiotic, an enzyme, an ionophore, a mycotoxin binder, an antiparasitic agent, an antibiotic, a herbal extract, a pigment, or combination thereof. The compound of Formula (I) has the following structure:

wherein:
R$^1$ is hydrocarbyl or substituted hydrocarbyl;
R$^2$ is hydrocarbyl or substituted hydrocarbyl;
Y is a cation chosen from hydrogen, ammonium, an alkali metal, an alkaline earth metal, or a transition metal;
Z is sulfur or selenium;
k is an integer of 1 or greater; and
n is an integer of 1 or greater.

Another aspect of the present disclosure encompasses a feed composition comprising at least one compound of Formula (I) and at least one nutritive agent. The compound of Formula (I) has the following structure:

wherein:
R$^1$ is hydrocarbyl or substituted hydrocarbyl;
R$^2$ is hydrocarbyl or substituted hydrocarbyl;
Y is a cation chosen from hydrogen, ammonium, an alkali metal, an alkaline earth metal, or a transition metal;
Z is sulfur or selenium;
k is an integer of 1 or greater; and
n is an integer of 1 or greater.

A further aspect of the present disclosure provides a method for inhibiting the growth of at least one microbe. The method comprises contacting the microbe with an effective amount of at least one compound of Formula (I). The compound of Formula (I) has the following structure:

wherein:
R$^1$ is hydrocarbyl or substituted hydrocarbyl;
R$^2$ is hydrocarbyl or substituted hydrocarbyl;
Y is a cation chosen from hydrogen, ammonium, an alkali metal, an alkaline earth metal, or a transition metal;
Z is sulfur or selenium;
k is an integer of 1 or greater; and
n is an integer of 1 or greater.

Other aspects and iterations of the present disclosure are presented below in more detail.

DETAILED DESCRIPTION

The present disclosure provides compositions and methods for inhibiting the microbial growth. It has been discovered that sulfur- or selenium-containing, fatty-acylated alpha-hydroxy acids or salts thereof have antimicrobial activity. Thus, these compounds or compositions comprising said compounds can be used as antimicrobial agents. The present disclosure, therefore, provides antimicrobial compositions comprising one or more of the compounds disclosed herein and at least one additional agent. Also provided herein are feed compositions comprising one or more of the compounds disclosed herein and at least one nutritive agent. Additionally, the present disclosure provides methods for using the compounds or compositions disclosed herein to inhibit microbial growth.

(I) Antimicrobial Compositions Comprising Compounds of Formula (I)

One aspect of the present disclosure provides antimicrobial compositions comprising at least one compound of Formula (I). The antimicrobial compositions further comprise at least one agent chosen from essential oils, metal chelates, minerals, amino acids, organic aids, vitamins, antioxidants, poly unsaturated fatty acids (PUFAs), prebiotics, probiotics, symbiotics, enzymes, ionophores, mycotoxin binders, antiparasitic agents, antibiotics, herbal extracts, pigments, or combinations thereof. The compositions may further comprise one or more excipients.

(a) Compounds of Formula (I)

(i) Structure

The compositions disclosed herein comprise at least one compound of Formula (I):

wherein:

$R^1$ is hydrocarbyl or substituted hydrocarbyl;

$R^2$ is hydrocarbyl or substituted hydrocarbyl;

Y is a cation chosen from hydrogen, ammonium, an alkali metal, an alkaline earth metal, or a transition metal;

Z is sulfur or selenium;

k is an integer of 1 or greater; and n is an integer of 1 or greater.

In some embodiments, Y is hydrogen and the compound of Formula (I) is a carboxylic acid of Formula (Ia):

wherein $R^1$, $R^2$, Z, k, and n are as defined above.

In other embodiments, Y is a cation other than hydrogen and the compound of Formula (I) is a carboxylate of Formula (Ib):

wherein $R^1$, $R^2$, Z, k, and n are as defined above, and M is a cation chosen from ammonium, an alkali metal, an alkaline earth metal, or a transition metal. Suitable metals include sodium, potassium, lithium, cesium, magnesium, calcium, manganese, cobalt, copper, zinc, iron, and silver. The ratio of the carboxylate of Formula (Ib) to the metal may range from about 1:1 to about 3:1. In specific embodiments, the cation may be sodium or potassium.

In various embodiments, $R^1$ may be unsubstituted or substituted alkyl, alkenyl, or aryl. In some embodiments, $R^1$ may be $C_1$ to $C_6$ alkyl or $C_1$ to $C_6$ alkenyl, wherein alkyl and alkenyl may be linear, branched, or cyclic. In certain embodiments, $R^1$ may be methyl, ethyl, propyl, isopropyl, butyl, tert-butyl, hexyl, cyclohexyl, and the like. In specific embodiments, $R^1$ may be methyl.

In certain embodiments, $R^2$ may be $C_4$ to $C_{30}$ alkyl, substituted $C_4$ to $C_{30}$ alkyl, $C_4$ to $C_{30}$ alkenyl, or substituted $C_4$ to $C_{30}$ alkenyl. The alkyl and alkenyl groups may be linear, branched, or cyclic, and the alkenyl groups may contain from one to six carbon-carbon double bonds. In some embodiments, $R^2$ may be $C_4$ to $C_{24}$ alkyl or $C_4$ to $C_{24}$ alkenyl, wherein the alkyl or alkenyl may be optionally substituted. In specific embodiments, $R^2$ may be $C_4$ to $C_{16}$ alkyl or $C_4$ to $C_{16}$ alkenyl, wherein the alkyl or alkenyl may be optionally substituted. For example, $R^2$ may be $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$ alkyl or alkenyl.

In some embodiments, Z may be sulfur. In other embodiments, Z may be selenium.

In various embodiments, k may range from 1 to several thousand. In some embodiments, k may range from 1 to 500, from 1 to 100, from 1 to 50, from 1 to 20, from 1 to 10, from 1 to 9, from 1 to 8, from 1 to 7, from 1 to 6, from 1 to 5, from 1 to 4, from 1 to 3, or from 1 to 2. In specific embodiments, k may range from 1 to 10.

In some embodiments, n may be an integer from 1 to 20, from 1 to 10, or from 1 to 6. In certain embodiments, n may be 1, 2, 3, or 4. In specific embodiments, n may be 2.

In exemplary embodiments, Y is hydrogen or an alkali metal, $R^1$ is methyl; $R^2$ is $C_4$ to $C_{16}$ alkyl, Z is sulfur, k is from 1 to 10, and n is 2.

(ii) Stereochemistry

The compounds of Formula (I) disclosed herein generally have at least one chiral center, as denoted with an asterisk in the schematic below wherein $R^1$, $R^2$, Y, Z, k, and n are as defined above. The compounds disclosed herein may comprise additional chiral centers.

Each chiral center may have an R or an S configuration. In compounds comprising one chiral carbon, the configuration may be R or S. In compounds comprising two or more chiral carbons, the configuration of each will be independently R or S. For example, in compounds comprising two chiral carbons, the configuration may be RR, RS, SR, or SS, in compounds comprising three chiral carbons, the configuration may be RRR, RRS, RSR, RSS, SRR, SRS, SSR, or SSS, and so forth.

(iii) Amount

The amount of the compounds of Formula (I) present in the composition can and will vary. In general, the weight fraction of the compounds of Formula (I) may range from 0.0001% to about 10% or more of the composition. In various embodiments, the weight fraction of the compounds of Formula (I) may range from about 0.0001% to about 0.0003%, from about 0.0003% to about 0.001%, from about 0.001% to about 0.003%, from about 0.003% to about 0.01%, from about 0.01% to about 0.03%, from 0.03% to about 0.1%, from about 0.1% to about 0.3%, from 0.3% to about 1%, from about 1% to about 3%, from about 3% to about 10%, or more than 10% of the composition.

(b) Other Components

The antimicrobial compositions disclosed herein further comprise at least one agent chosen from essential oils, metal chelates, minerals, amino acids, organic acids, vitamins, antioxidants, poly unsaturated fatty acids (PUFAs), prebiotics, probiotics, symbiotics, enzymes, ionophores, mycotoxin binders, antiparasitic agents, antibiotics, herbal extracts, pigments, or combinations thereof. The antimicrobial compositions may also include one or more excipients.

(i) Essential Oils

In some embodiments, the antimicrobial composition may comprise at least one essential oil or derivative thereof. The essential oil or derivative thereof may have antimicrobial activity. Non-limiting examples of suitable essential oils include (presented with scientific name of the plant from which it is derived and active ingredients): ajwain (*Trachyspermum ammi*; thymol), aniseed (*Pimpinella anisum*; α-pinene, camphene, β-pinene, linalool, cis-anethole, trans-anethole, safrole, anisaldehyde, acetoanisole), basil (*Ocimum basilicum*; linalool, methylchavikol, methylcinnamat, linolen), calamus (*Acorus calamus*; α-asarone, β-asarone, eugenol), capsicum (*Capsicum annuum, Capsicum frutescen*; capsaicin, capsaicinoids); caraway (*Carum carvi*; carvone, limonene, thymol, carvacrol, eugenol), cardamon (*Elettaria cardomomum*; α-pinene, β-pinene, sabinene, myrcene, α-phellandrene, limonene, 1,8-cineole, y-terpinene, p-cymene, terpinolene, linalool, linalyl acetate, terpinen-4-oil, α-terpineol, α-terpineol acetate, citronellol, nerol, geraniol, methyl eugenol, trans-nerolidol), chamomile (*Matricaria*; terpene bisabolol, farnesene, chamazulene, flavonoids (including apigenin, quercetin, patuletin and luteolin), coumarin), chervil (*Anthriscus cerefolium*; methyl chavicol), chrysanthemum (*Chrysanthemum indicum*; limonene, β-farnesene, 1,8-cineole, camphor, borneol, bornyl acetate), cinnamon (*Cinnamomum zeylanicum*; cinnamaldehyde, ethyl cinnamate, eugenol, beta-caryophyllene, linalool, methyl chavicol0, citron (*Citrus sinensis* fruit; limonene), clove (*Syzygium aromaticum*; eugenol, eugenyl acetate, caryophyllene), coriander (*Coriandrum sativum*; linalool, neryl acetate, γ-terpinene, α-pinene), dill (*Anethum graveolens*; d-carvone, dill apiol, eugenol, limonene, terpinene, myristicin), eucalyptus (*Eucalyptus globulus*; cineole, piperitone, phellandrene, citral, methyl cinnamate, geranyl acetate), garlic (*Allium sativum*; alliin, ajoene, diallyl polysulfides, vinyldithiins, S-allylcysteine), geranium (Rose *Pelargonium x asperum*; tannins such as gallic acid and flavone), gGinger (*Zingiber officinale*; (6)-gingerol, (6)-shagaol, (6)- and (10)-dehyro-gingerdione, (6)- and (10)-gingerdione, (6)-paradol, vallinoids, galanals A and B, zingerone), grapefruit (*citrus paradisi*; α-pinene, sabinene, myrcene, limonene, geraniol, linalool, citronellal, decyl acetate, neryl acetate, terpinen-4-ol), honeysuckle (various varieties; linalool, ocimene, farnesene, germacrene D, eugenol, vanillin, (−)-methyl jasmonate, (+)-epi-methyl jasmonate, jasmone, (−)-jasmin lactone), juniper (*Juniperus Communis*; α-pinene, camphene, β-pinene, sabinene, myrcene, α-phellandrene, α-terpinene, ψ-terpinene, 1,4-cineole, β-phellandrene, p-cymene, terpinen-4-ol, bornyl acetate, cayophyllene, limonene, camphor, linalool, linalyl acetate, borneol, nerol), lavender, lemon (*Citrus x limon*; dl-limonene, α-pinene, I-α-terpineol, β-myrcene, β-pinene, β-linalool, α-terpinolene, terpinen-4-ol, cymene, E-citral). lemon balm (*Melissa officinalis*; eugenol, tannins, terpenes), lemongrass (*Cymbopogon citratus*; citral, myrcene, citronella, citronellol, geranilol), lime (*Citrus aurantifolia, C. latifoli*; d-limonene, beta-pinene, gamma-terpinene, citral), marjoram (*Origanum majorana*; thymol, sabinene, a terpinene, gamma terpinene, cymene, terpinolene, linalool, sabinene hydrate, linalyl acetate, terpineol, gamma terpineol), mint (*mentha spicata*; menthol, menthone, menthyl acetate, menthofuran, 1,8-cineol), mustard oil (*Brassica nigra, B. juncea*; allylisothiocyanate, erucic acid, oleic acid, omega-3 alpha-linolenic acid, omega-6 linoleic acid), nutmeg (*Myristica fragrans*; myristicin, elemicin), oregano (*Origanum vulgare*; carvacrol, thymol, limonene, pinene, ocimene, caryophyllene), palmarosa (*Cymbopogon martini*; myrcene, linalool, geraniol, geranyl acetate, dipentene, limonene), peppermint (*Mentha x piperita*; menthol, menthone, methyl acetate, menthofuran, 1,8-cineol), rose (*Rosa damascena*; citronellol, geraniol, nerol, linalool, phenyl ethyl alcohol, farnesol, stearoptene, α-pinene, β-pinene, α-terpinene, limonene, p-cymene, camphene, β-caryophyllene, neral, citronellyl acetate, geranyl acetate, neryl acetate, eugenol, methyl eugenol, rose oxide, α-damascenone, β-damascenone, benzaldehyde, benzyl alcohol, rhodinyl acetate, phenyl ethyl formate); rosemary (*Rosmarinus officinalis*; rosmarinic acid, camphor, caffeic acid, ursolic acid, betulinic acid, carnosic acid, carnosol), saffron (*Crocus sativus*; zeaxanthin, lycopene, α- and β-carotenes, picrocrocin, safranal, α-crocin), sage (*Salvia officinalis*; α-pinene, camphene, β-pinene, myrcene, limonene, 1,8-cineole, α-thujone, β-thujone, camphor, linalool, bornyl acetate, borneol), savory (*Satureja montana, S. hortensis*; carvarol, terpinene, paracymene, linalool, terpeneol, borneol), shiitake mushroom (*Lentinula edodes*; lentinan), tarragon (*Artemisia dracunculus*; methyl chavicol, methyl eugenol, trans-anethole, α-trans-ocimene, limonene, α-pinene, allo-ocimene, methyl eugenol, β-pinene, α-terpinolene), tea-tree oil (*Melaleuca alternifolia*; terpinen-4-ol, terpinolene, 1,8-cineole), thyme (*Thymus vulgaris*: thymol, p-cymene, myrcene, borneol, linalool), tumeric (*Curcuma longa*; curcumin, demethoxycurcumin, bisdemethoxycurcumin, turmerone, atlantone, zingiberene), and vetiver (*Chrysopogon zizanioides*; benzoic acid, vetiverol, furfurol, a and b-vetivone, vetivene vetivenyl vetivenate). In specific embodiments, the essential oil may be cinnamon oil, lavender oil, oregano oil, rosemary oil, thyme oil, extracts thereof, or combinations thereof.

(ii) Metal Chelates

In other embodiments, the antimicrobial composition may comprise at least one metal chelate. A metal chelate comprises at least one metal ion and a chelating ligand. The chelating agent may be an amino acid or derivative thereof, an organic acid or derivative thereof, or a monosaccharide or derivative thereof, a protein or derivative thereof (e.g., hydrolysate), or a multidentate ligand (such as ethylene diamine). In embodiments in which the chelate comprises an amino acid, the amino acid may be alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine or their hydroxy analogs. Suitable organic acids include without limit ascorbic acid, citric acid, fumaric acid, gallic acid, gluconic acid, lactic acid, malic acid, succinic acid, and the like. The metal ion may be zinc, copper, magnesium, manganese, iron, chromium, selenium, calcium, or combinations thereof. The ratio of ligand to metal ion in the chelate molecule may generally vary from 1:1 to 3:1 or higher. Typically, a metal chelate may comprise a mixture of 1:1, 2:1 and 3:1 species. Preferably, the ratio of ligand to metal ion in the chelate molecule may generally vary from 1.5:1 to 2.5:1.

In embodiments in which the ligand is an amino acid and when the number of ligands equates to the charge on the metal ion, the charge is typically balanced because the carboxyl moieties of the amino acids are in deprotonated form. For example, in the chelate species wherein the metal cation carries a charge of 2+ and the amino acid to metal ratio is 2:1, each of the hydroxyl or amino groups is understood to be bound by a coordinate covalent bond to the metal while an ionic bond prevails between each of the carboxylate groups and the metal ion. Where the number of ligands exceeds the charge on the metal ion, e.g., in a 3:1 chelate of a divalent metal ion, the amino acids in excess of the charge typically may remain in a protonated state to balance the charge. On the other hand, where the positive charge on the metal ion exceeds the number of amino acids, the charge may be balanced by the presence of another anion such as, for example, chloride, bromide, iodide, bicarbonate, hydrogen sulfate, dihydrogen phosphate and combinations thereof. Divalent anions may also be present.

(iii) Minerals

In further embodiments, the antimicrobial composition may include one or more minerals or mineral sources. Non-limiting examples of minerals include, without limitation, calcium, iron, chromium, copper, iodine, zinc, magnesium, manganese, molybdenum, phosphorus, potassium, and selenium. Suitable forms of any of the foregoing minerals include soluble mineral salts, slightly soluble mineral salts, insoluble mineral salts, chelated minerals, mineral complexes, non-reactive minerals such as carbonyl minerals, and reduced minerals, and combinations thereof. Non-limiting examples of suitable mineral salts include carbonates, halides, phosphates, gluconate, sulfates, nitrates, oxides, acetates, alginates, ascorbates, caprylates, citrates, formates, glutarates, glycerophosphates, lactates, malates, oxalates, succinates, tartrates, and the like.

(iv) Amino Acids

In additional embodiments, the antimicrobial composition may comprise at least one amino acid. The amino acid may be natural, synthetic, substituted (e.g., alpha hydroxy, N-acylated), proteinogenic, or non-proteinogenic (e.g., carnitine, selenomethionine, hydroxyproline, etc.). Suitable proteinogenic amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, alpha hydroxy or N-acyl analogs thereof, or physiologically acceptable salts thereof. In certain embodiments, the amino acid will be selected from the essential amino acids. An essential amino acid is generally described as one that cannot be synthesized de novo by the organism, and therefore, must be provided in the diet. By way of non-limiting example, the essential amino acids for humans include: L-histidine, L-isoleucine, L-leucine, L-lysine, L-methionine, L-phenylalanine, L-valine and L-threonine. In other embodiments, the amino acid derivative may be an alpha hydroxy acid.

(v) Organic Acids

In some other embodiments, the antimicrobial composition may comprise one or more organic acids or salts thereof. In one embodiment, the organic acid may contain from about one to about twenty-five carbon atoms. In another embodiment, the organic acid may have from about three to about twenty-two carbon atoms. In a further embodiment, the organic acid may contain from about three to about twelve carbon atoms. In yet another embodiment, the organic acid may contain from about eight to about twelve carbon atoms. In still another embodiment, the organic acid may contain from about two to about six carbon atoms. Suitable organic acids, by way of non-limiting example, include acetic acid, adipic acid, benzoic acid, boric acid, butanoic acid, cinnamaldehyde, citric acid, formic acid, fumaric acid, glutaric acid, glycolic acid, lactic acid, mandelic acid, malic acid, maleic acid, malonic acid, propionic acid, sorbic acid, succinic acid, and tartaric acid. Representative suitable salts include the ammonium, magnesium, calcium, lithium, sodium, potassium, selenium, iron, copper, and zinc salts of organic acids.

(vi) Vitamins

In still other embodiments, the antimicrobial composition may include one or more vitamins. Suitable vitamins include vitamin A, vitamin B1, vitamin B2, vitamin B3, vitamin B5, vitamin B6, vitamin B7, vitamin B9, vitamin B12, vitamin C, vitamin D, vitamin E, and vitamin K. The form of the vitamin may include salts of the vitamin, derivatives of the vitamin, compounds having the same or similar activity of a vitamin, and metabolite derivatives of a vitamin.

(vii) Antioxidants

In yet further embodiments, the antimicrobial composition may include one or more suitable antioxidants. Non limiting examples of suitable antioxidants include ascorbic acid and its salts, ascorbyl palmitate, ascorbyl stearate, anoxomer, N-acetylcysteine, benzyl isothiocyanate, o-, m- or p-amino benzoic acid (o is anthranilic acid, p is PABA), butylated hydroxyanisole (BHA), butylated hydroxytoluene (BHT), caffeic acid, canthaxantin, alpha-carotene, beta-carotene, beta-caraotene, beta-apo-carotenoic acid, carnosol, carvacrol, catechins, cetyl gallate, chlorogenic acid, citric acid and its salts, p-coumaric acid, curcurin, 3,4-dihydroxybenzoic acid, N,N'-diphenyl-p-phenylenediamine (DPPD), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline, ethyl gallate, ethyl maltol, ethylenediaminetetraacetic acid (EDTA), eugenol, ferulic acid, flavonoids, flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinnammic acid, hydroxyglutaric acid, hydroquinone, N-hydroxysuccinic acid, hydroxytryrosol, hydroxyurea, lactic acid and its salts, lecithin, lecithin citrate; R-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (NDGA), octyl gallate, oxalic acid, palmityl citrate, phenothiazine, phosphatidylcholine, phosphoric acid, phosphates, phytic acid, phytylubichromel, propyl gallate, polyphosphates, quercetin, trans-resveratrol, rosmarinic acid, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanilic acid, 2,6-di-tert-butyl-4-hydroxymethylphenol (i.e., lonox 100), 2,4-(tris-3',5'-bi-tert-butyl-4'-hydroxybenzyl)-mesitylene (i.e., lonox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivates, vitamin Q10, zeaxanthin, or combinations thereof.

Natural antioxidants that may be included in the antimicrobial composition include, but are not limited to, apple peel extract, blueberry extract, carrot juice powder, clove extract, coffeeberry, coffee bean extract, cranberry extract, *eucalyptus* extract, ginger powder, grape seed extract, green tea, olive leaf, parsley extract, peppermint, pimento extract, pomace, pomegranate extract, rice bran extract, rosehips, rosemary extract, sage extract, tart cherry extract, tomato extract, tumeric, and wheat germ oil.

(viii) PUFAs

In some embodiments, the antimicrobial composition may include one or more PUFAs. Suitable PUFAs include a long chain fatty acid with at least 18 carbon atoms and at least two carbon-carbon double bonds, generally in the cis-configuration. In an exemplary embodiment, the PUFA is an omega fatty acid. The PUFA may be an omega-3 fatty acid in which the first double bond occurs in the third carbon-carbon bond from the methyl end of the carbon chain (i.e., opposite the carboxyl acid group). Suitable examples of omega-3 fatty acids include all-cis 7,10,13-hexadecatrienoic acid; all-cis-9,12,15-octadecatrienoic acid (alpha-linolenic acid, ALA); all-cis-6,9,12,15,-octadecatetraenoic acid (stearidonic acid); all-cis-8,11,14,17-eicosatetraenoic acid (eicosatetraenoic acid); all-cis-5,8,11,14,17-eicosapentaenoic acid (eicosapentaenoic acid, EPA); all-cis-7,10,13,16,19-docosapentaenoic acid (clupanodonic acid, DPA); all-cis-4,7,10,13,16,19-docosahexaenoic acid (docosahexaenoic acid, DHA); all-cis-4,7,10,13,16,19-docosahexaenoic acid; and all-cis-6,9,12,15,18,21-tetracosenoic acid (nisinic acid). In an alternative embodiment, the PUFA may be an omega-6 fatty acid in which the first double bond occurs in the sixth carbon-carbon bond from the methyl end of the carbon chain. Examples of omega-6 fatty acids include all-cis-9,12-octadecadienoic acid (linoleic acid); all-cis-6,9,12-octadecatrienoic acid (gamma-linolenic acid, GLA); all-cis-11,14-eicosadienoic acid (eicosadienoic acid); all-cis-8,11,14-eicosatrienoic acid (dihomo-gamma-linolenic acid, DGLA); all-cis-5,8,11,14-eicosatetraenoic acid (arachidonic acid, AA); all-cis-13,16-docosadienoic acid (docosadienoic acid); all-cis-7,10,13,16-docosatetraenoic acid (adrenic acid); and all-cis-4,7,10,13,16-docosapentaenoic acid (docosapentaenoic acid). In yet another alternative embodiment, the PUFA may be an omega-9 fatty acid in which the first double bond occurs in the ninth carbon-carbon bond from the methyl end of the carbon chain, or a conjugated fatty acid, in which at least one pair of double bonds are separated by only one single bond. Suitable examples of omega-9 fatty acids include cis-9-octadecenoic acid (oleic acid); cis-11-eicosenoic acid (eicosenoic acid); all-cis-5,8,11-eicosatrienoic acid (mead acid); cis-13-docosenoic acid (erucic acid), and cis-15-tetracosenoic acid (nervonic acid). Examples of conjugated fatty acids include 9Z,11E-octadeca-9,11-dienoic acid (rumenic acid); 10E,12Z-octadeca-9,11-dienoic acid; 8E,10E,12Z-octadecatrienoic acid (α-calendic acid); 8E,10E,12E-octadecatrienoic acid (β-Calendic acid); 8E,10Z,12E-octadecatrienoic acid (jacaric acid); 9E,11E,13Z-octadeca-9,11,13-trienoic acid (α-eleostearic acid); 9E,11E,13E-octadeca-9,11,13-trienoic acid (β-eleostearic acid); 9Z,11Z,13E-octadeca-9,11,13-trienoic acid (catalpic acid), and 9E,11Z,13E-octadeca-9,11,13-trienoic acid (punicic acid).

(ix) Prebiotics, Probiotics, Synbiotics

In other embodiments, the antimicrobial composition may include one or more prebiotics, one or more probiotics, or combinations of both (i.e., symbiotics). Probiotics and prebiotics may include yeast and bacteria that help establish an immune protective rumen or gut microflora as well as small oligosaccharides. By way of non-limiting example, yeast-derived probiotics and prebiotics include yeast cell wall derived components such as β-glucans, arabinoxylan isomaltose, agarooligosaccharides, lactosucrose, cyclodextrins, lactose, fructooligosaccharides, laminariheptaose, lactulose, β-galactooligosaccharides, mannanoligosaccharides, raffinose, stachyose, oligofructose, glucosyl sucrose, sucrose thermal oligosaccharide, isomalturose, caramel, inulin, and xylooligosaccharides. In a specific embodiment, the yeast-derived agent may be β-glucans and/or mannanoligosaccharides. Sources for yeast cell wall derived components include *Saccharomyces bisporus, Saccharomyces boulardii, Saccharomyces cerevisiae, Saccharomyces capsularis, Saccharomyces delbrueckii, Saccharomyces fermentati, Saccharomyces lugwigii, Saccharomyces microellipsoides, Saccharomyces pastorianus, Saccharomyces rosei, Candida albicans, Candida cloaceae, Candida tropicalis, Candida utilis, Geotrichum candidum, Hansenula americana, Hansenula anomala, Hansenula wingei*, and *Aspergillus oryzae*.

Probiotics and prebiotics may also include bacteria cell wall derived agents such as peptidoglycan and other components derived from gram-positive bacteria with a high content of peptidoglycan. Exemplary gram-positive bacteria include *Lactobacillus acidophilus, Bifedobact thermophilum, Bifedobat longhum, Streptococcus faecium, Bacillus pumilus, Bacillus subtilis, Bacillus licheniformis, Bacillus amyloliquefaciens, Lactobacillus acidophilus, Lactobacillus casei, Enterococcus faecium, Bifidobacterium bifidium, Propionibacterium acidipropionici, Propionibacteriium freudenreichii*, and *Bifidobacterium pscudolongum*.

(x) Enzymes

In still other embodiments, the antimicrobial composition may comprise one or more enzymes. Non-limiting examples of suitable enzymes include phytases, proteases, carbohydrases, xylanases, beta-glucanases, alpha-galactosidases, cellulases, alpha-amylases, beta-amylases, lipases, mannanases, cellulases, pectinases, hemicellulasepectinases, and variants thereof. The enzyme can be wild type, modified, or engineered. The enzyme can be derived from bacterial, fungal, or animal sources. The enzyme can be recombinantly produced.

(xi) Ionophores

In alternate embodiments, the antimicrobial composition may comprise one or more ionophores. Suitable ionophores include but are not limited to bambermycin, decoquiate, declazuril, lasalocid, maduramicin, monensin, narasin, nicarazin, nystatin, robenedine, salinomycin, semduramicin, variants, or derivatives thereof.

(xii) Mycotoxin Binders

In yet other embodiments, the antimicrobial composition may comprise one or more mycotoxin binders. Examples of suitable mycotoxin binders include, without limit, charcoal, activated carbon, silicates (e.g., phyllosilicates, tectosilicates, aluminosilicates, hydrated sodium calcium aluminosilicates, bentonites, zeolites, clinoptilolites, montmorillonites, and modified versions thereof), organic polymers (e.g., cellulose, glucomannans, peptidoglycans, and modified versions thereof), synthetic polymers (e.g., cholestyramine, polyvinylpyrrolidone, and the like), yeast cell wall extracts, and bacterial extracts.

(xiii) Antiparasitic Agents

In further embodiments, the antimicrobial composition may comprise one or more antiparasitic agents. Examples of suitable antiparasitic agents include but are not limited to abamectn, afloxolaner, albendazole, alphamethrin, amitraz, azamethiphos, carbaryl, chlorfenvinphos, chlorpyrifos, clorsulon, closantel, coumaphos, cyfluthrin, cyhalothrin, cymiazol, cypermethrin, cyromazine, ceclorcos, deltamethrin, diazinon, dichlorvos, dicyclanil, diflubenzuron, doramectin, dympilate, eprinomectin, ethion, febtantel, fenbendazole, fenitrothion, fenthion, fenvalerate, fipronil, fluazuron, flubendazole, flumethrin, imidacloprid, ivermectin, levamisole, lufenuron, malathion, mebendazole, metrifonate, methoprene, milbemycin oxime, monepantel, morantal, moxidectin, netobimin, niclosamide, nitroxinil, oxfendazole, oxibendazole, oxyclozanide, permethrin, phosmet, phoxim, piperazine, praziquantel, propoxur, pyrantel, rafoxanide, ribobendazole, rofenone, selamectin, spinosad, trichlorfon, thiabendazole, thiamethoxam, thiophanate, triclabendazole, and triflumuron.

(xiv) Approved Antibiotics

In other embodiments, the antimicrobial composition may comprise one or more antibiotics approved for use in livestock and poultry (i.e., antibiotics not considered critical or important for human health). Non-limiting examples of approved antibiotics include bacitracin, carbadox, ceftiofur, enrofloxacin, florfenicol, laidlomycin, linomycin, oxytetracycline, roxarsone, tilmicosin, tylosin, and virginiamycin.

(xv) Herbal Extracts

In still other embodiments, the antimicrobial composition may comprise one or more herbal extracts or derivatives thereof. Herbals, herbal extracts, and derivatives thereof refer to extracts and substances derived from plants and plant parts, such as leaves, flowers and roots, without limitation. Non-limiting exemplary herbals or herbal extracts include agrimony, alfalfa, aloe vera, amaranth, angelica, anise, barberry, basil, bayberry, bee pollen, birch, bistort, blackberry, black cohosh, black walnut, blessed thistle, blue cohosh, blue vervain, boneset, borage, buchu, buckthorn, bugleweed, burdock, *capsicum*, cayenne, caraway, cascara sagrada, catnip, celery, centaury, chamomile, chaparral, chickweed, chicory, chinchona, cloves, coltsfoot, comfrey, cornsilk, couch grass, cramp bark, culver's root, cyani, cornflower, damiana, dandelion, devils claw, dong quai, echinacea, elecampane, ephedra, *eucalyptus*, evening primrose, eyebright, false unicorn, fennel, fenugreek, figwort, flaxseed, garlic, gentian, ginger, ginseng, golden seal, gotu kola, gum weed, hawthorn, hops, horehound, horseradish, horsetail, hoshouwu, hydrangea, hyssop, iceland moss, irish moss, jojoba, juniper, kelp, lady's slipper, lemon grass, licorice, lobelia, mandrake, marigold, marjoram, marshmallow, mistletoe, mullein, mustard, myrrh, nettle, oatstraw, oregon grape, papaya, parsley, passion flower, peach, pennyroyal, peppermint, periwinkle, plantain, pleurisy root, pokeweed, prickly ash, psyllium, quassia, queen of the meadow, red clover, red raspberry, redmond clay, rhubarb, rose hips, rosemary, rue, safflower, saffron, sage, St. John's wort, sarsaparilla, sassafras, saw palmetto, scullcap, senega, senna, shepherd's purse, slippery elm, spearmint, spikenard, squawvine, stillingia, strawberry, taheebo, thyme, uva ursi, valerian, violet, watercress, white oak bark, white pine bark, wild cherry, wild lettuce, wild yam, willow, wintergreen, witch hazel, wood betony, wormwood, yarrow, yellow dock, yerba santa, yucca, and combinations thereof.

(xvi) Pigments

In yet alternate embodiments, the antimicrobial composition comprises one or more pigments or derivatives thereof. Suitable non-limiting pigments include actinioerythrin, alizarin, alloxanthin, $\beta$-apo-2'-carotenal, apo-2-lycopenal, apo-6'-lycopenal, astacein, astaxanthin, azafrinaldehyde, aacterioruberin, aixin, $\alpha$-carotine, $\beta$-carotine, $\gamma$-carotine, $\beta$-carotenone, canthaxanthin, capsanthin, capsorubin, citranaxanthin, citroxanthin, crocetin, crocetinsemialdehyde, crocin, crustaxanthin, cryptocapsin, $\alpha$-cryptoxanthin, $\beta$-cryptoxanthin, cryptomonaxanthin, cynthiaxanthin, decaprenoxanthin, dehydroadonirubin, diadinoxanthin, 1,4-diamino-2,3-dihydroanthraquinone, 1,4-dihydroxyanthraquinone, 2,2'-Diketospirilloxanthin, eschscholtzxanthin, eschscholtzxanthone, flexixanthin, foliachrome, fucoxanthin, gazaniaxanthin, hexahydrolycopene, hopkinsiaxanthin, hydroxyspheriodenone, isofucoxanthin, loroxanthin, lutein, luteoxanthin, lycopene, lycopersene, lycoxanthin, morindone, mutatoxanthin, neochrome, neoxanthin, nonaprenoxanthin, OH-Chlorobactene, okenone, oscillaxanthin, paracentrone, pectenolone, pectenoxanthin, peridinin, phleixanthophyll, phoeniconone, phoenicopterone, phoenicoxanthin, physalien, phytofluene, pyrrhoxanthininol, quinones, rhodopin, rhodopinal, rhodopinol, rhodovibrin, rhodoxanthin, rubixanthone, saproxanthin, semi-$\alpha$-carotenone, semi-$\beta$-carotenone, sintaxanthin, siphonaxanthin, siphonein, spheroidene, tangeraxanthin, torularhodin, torularhodin methyl ester, torularhodinaldehyde, torulene, 1,2,4-trihydroxyanthraquinone, triphasiaxanthin, trollichrome, vaucheriaxanthin, violaxanthin, wamingone, xanthin, zeaxanthin, $\alpha$-zeacarotene, and combinations thereof.

(xvii) Excipients

The antimicrobial composition also may comprise one or more excipients. Suitable excipients include fillers, diluents, binders, pH modifiers, anti-caking agents, disintegrants, lubricants, dispersants, preservatives, flavoring agents, sweetening agents, taste masking agents, coloring agents, and combinations thereof.

Suitable fillers include, without limit, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, and sorbitol.

Diluents suitable for inclusion include saccharides such as sucrose, dextrose, lactose, microcrystalline cellulose, fructose, xylitol, and sorbitol, polyhydric alcohols, starches, pre-manufactured direct compression diluents, and mixtures of any of the foregoing.

Non-limiting examples of suitable binders include starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof. The polypeptide may be any arrangement of amino acids ranging from about 100 to about 300,000 daltons.

Suitable pH modifiers include sodium carbonate, sodium bicarbonate, citric acid, tartaric acid, and the like.

Examples of anti-caking agents include magnesium stearate, magnesium sulfate, magnesium oxide, sodium bicarbonate, sodium silicate, silicon dioxide, talc, and combinations thereof.

Suitable disintegrants include, without limit, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, tragacanth, and combinations thereof.

Non-limiting examples of lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

Suitable dispersants include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

Suitable examples of preservatives include, but are not limited to, antioxidants, such as a-tocopherol or ascorbate, and antimicrobials, such as parabens, chlorobutanol or phenol.

Flavoring agents may be chosen from synthetic flavor oils and flavoring aromatics and/or natural oils, extracts from plants, leaves, flowers, fruits, and combinations thereof. By way of example, these may include cinnamon oils, oil of wintergreen, peppermint oils, clover oil, hay oil, anise oil, *eucalyptus*, vanilla, *citrus* oil, such as lemon oil, orange oil, grape and grapefruit oil, fruit essences including apple, peach, pear, strawberry, raspberry, cherry, plum, pineapple, and apricot.

Suitable sweetening agents glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; Stevia Rebaudiana (Stevioside); chloro derivatives of sucrose such as sucralose; sugar alcohols such as sorbitol, mannitol, sylitol, and the like.

Taste-masking agents include cellulose hydroxypropyl ethers, low-substituted hydroxypropyl ethers, cellulose hydroxypropyl methyl ethers, alkylcelluloses, hydroxy- or carboxy-substituted alkyl celluloses, acrylic polymers, cellulose acetate phthalate, cyclodextrins, and mixtures thereof.

Suitable color agents include food, drug and cosmetic colors (FD&C), drug and cosmetic colors (D&C), or external drug and cosmetic colors (Ext. D&C). These colors or dyes, along with their corresponding lakes, and certain natural and derived colorants may be suitable for use in the present composition depending on the embodiment.

(xiii) Amount

The weight fraction of the other components in the antimicrobial composition may be about 99% or less, about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

(c) Physical Form

In various embodiments, the antibiotic composition disclosed herein may be a powder, a granular mixture, a pelleted mixture, a solid form such as a tablet or capsule, a liquid solution, an aqueous solution, an emulsion, a gel, or a paste.

(II) Feed Compositions Comprising Compounds of Formula (I)

Another aspect of the present disclosure encompasses feed compositions comprising at least one compound of Formula (I) and at least one nutritive agent.

(a) Compounds of Formula (I)

Compounds of Formula (I) are detailed above in section (I)(a).

(b) Nutritive Agents

The nutritive agent may be a carbohydrate source, a fat source, a protein source, an amino acid or derivative thereof, or combination thereof.

Suitable carbohydrate sources may be chosen from those known in the art and include, without limitation, alginate, arrowroot, barley, canola, cassava, corn, corn syrup, cottonseed meal, fructose, glucose, galactose, grain sorghum, kelp meal, lactose, maize, maltose, mannose, potatoes, oats, rice, rye, sago, sorbitol, soybeans, tapioca, wheat, wheat gluten, yam, and combinations thereof.

The fat source may be an inert fat or a non-inert fat. Non-limiting examples of non-inert fats include plant derived oils (e.g., canola oil, corn oil, cottonseed oil, palm oil, peanut oil, safflower oil, soybean oil, and sunflower oil), fish oils (e.g., menhaden oil, anchovy oil, albacore tuna oil, cod liver oil, herring oil, lake trout oil, mackerel oil, salmon oil, and sardine oil), animal fats (e.g., poultry fat, beef tallow, butter, pork lard, and whale blubber), yellow grease (i.e., waste grease from restaurants and low-grade fats from rendering plants), and combinations thereof. The non-inert fat source may also be a high fat product such as fish meal (e.g., menhaden meal, anchovy meal, herring meal, pollack meal, salmon meal, tuna meal, and whitefish meal), oilseeds (e.g., canola seeds, cottonseeds, flax seeds, linseeds, Niger seeds, sesame seeds, soy beans, and sunflower seeds), or distillers grains (e.g., dried distillers grains and solubles (DDGS) and wet distillers grains). The fat source may be a ruminally inert fat. Suitable examples of ruminally inert fats include calcium salts of palm fatty acids (e.g., MEGA-LAC®), saturated free fatty acids, or hydrogenated tallow (e.g., ALIFET®).

Suitable protein sources may be animal-derived proteins, plant-derived proteins, algal-derived proteins, or combinations thereof. In some embodiments, suitable sources of animal derived protein include blood meal, bone meal, fish meal, fish processing by-products, meat meal, meat and bone meal, poultry by-produce meal, feather meal, and combinations thereof. In other embodiments, suitable sources of plant-derived proteins include grains such as corn, oats, soybean, and the like; grain protein concentrates such as soy protein concentrate; legumes such as peas, lupine, alfalfa; distiller's grains; oilseed meals such as canola meal, cottonseed meal, flaxseed meal, soybean meal, sunflower seed meal; and combinations thereof.

Suitable amino acids or derivatives thereof are described above in section (I)(b)(iv). In one embodiment, the amino acid derivative may be an alpha hydroxy acid.

The weight fraction of the nutritive agent(s) in the feed composition may be about 99% or less, about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The feed composition may also comprise at least one agent chosen from essential oils, metal chelates, minerals, amino acids, organic acids, vitamins, antioxidants, poly unsaturated fatty acids (PUFAs), prebiotics, probiotics, symbiotics, enzymes, ionophores, mycotoxin binders, antiparasitic agents, antibiotics, herbal extracts, pigments, excipients, or combinations thereof, which are detailed above in sections (I)(b)(i)-(xvii).

The feed composition may be formulated as a powder, a granular mixture, a pelleted mixture, or a liquid.

(III) Methods for Inhibiting Microbial Growth

A further aspect of the present disclosure provides methods for inhibiting the growth of at least one microbe. The method comprises contacting the microbe with an effective amount of at least one compound of Formula (I). Compounds of Formula (I) are detailed above in section (I)(a). In some embodiments, the method comprises contacting the microbe with a composition comprising at least one compound of Formula (I). Antimicrobial compositions comprising compounds of Formula (I) are detailed above in section (I) and feed compositions comprising compounds of Formula (I) are detailed above in section (II). Persons skilled in the art are familiar with means for determining an effective amount of compounds of Formula (I) or a composition comprising compounds of Formula (I).

Suitable microbes generally include bacteria. In specific embodiments, the microbe may be a gram positive bacterium such as, e.g., *Clostridium* (e.g., *C. perfringens*), *Bacillus, Lactobacillus, Listeria, Corynebacterium, Enterococcus, Staphylococcus, Streptococcus*, and so forth. In other embodiments, the microbe may be a gram negative bacterium such as, e.g., *Escherichia* (e.g., *E. coli*), *Salmonella, Camplybacter, Pseudomonas*, and *Desulfovibrionales* (e.g., *Lawsonia*). In certain embodiments, the microbe may be part of or embedded in a biofilm.

The identity of the subject can and will vary. Suitable subjects include, without limit, humans, swine (such as domestic pigs, wild pigs, wild boars), poultry (such as chickens turkeys, ducks, and geese, ruminants (such as dairy cows, beef cattle, veal, sheep, goats, bison, deer, and elk), aquatic organisms (such as fish and crustaceans including, but not limited to, salmon, shrimp, carp, tilapia and shell fish), companion animals (such as cats, dogs, rabbits, horses, rats, gerbils, and so forth), zoo animals, research animals, and the like.

In some embodiments, the microbe may be within the digestive tract (i.e., any alimentary canal organ) of a subject and the compound of Formula (I) may be administered orally. The compound of Formula (I) may be either in a dry form or a liquid form. The compound may be administered as part of a composition, an antimicrobial composition, a feed composition, a feed premix, a feed supplement, a feed blend, a diet additive, a diet supplement, a water supplement, or the like. The compound may be administered one time, two times, or three times a day.

In other embodiments, the microbe may be on a surface of a subject and the compounds of Formula (I) may be applied topically. For example, the compounds of Formula (I) or composition comprising the compounds may be applied to a skin surface or mucosal membrane surface of the subject.

Subjects administered the compounds of Formula (I), orally or topically, may exhibit beneficial effects. Beneficial effects include reduced levels of pathogenic microorganisms, increased levels of beneficial microorganisms, increased nutrient uptake, increased digestion, increased feed efficiency, improved intestinal barrier function, reduced enteritis, increased innate immunity, increased immune response, increased weight gain, increased performance index, improved feed conversion ratio, or combinations thereof. Persons of skill in the art are familiar with means for measuring any of the above-listed parameters.

In alternate embodiments, the microbe may be within or on a surface of an inanimate object. Non-limiting examples of suitable inanimate objects include food or feed, food or feed products (e.g., pet food, pet treats), food or feed preparation equipment, food or feed packing material, health care equipment, medical devices (e.g., catheters, cardiac devices, orthopedic devices, tubes, implants, surgical equipment, etc.) and packaging for household, healthcare, or industrial products.

(IV) Processes for the Preparation of Compounds of Formula (I)

Also provided herein are processes for preparing the compounds of Formula (I). As detailed above in section (I), compounds in which Y is hydrogen have Formula (Ia) and compounds in which Y is cation other than hydrogen have Formula (Ib). Persons skilled in the art understand that a variety of different processes may be used to prepare the compounds disclosed herein. Exemplary processes are described below.

(a) Preparation of Compounds of Formula (Ia)

The process comprises contacting compounds of Formula (II) with an acyl halide, $R^2C(O)X$, to form compounds of Formula (Ia) according to the following reaction scheme:

wherein $R^1$, $R^2$, Z, k, and n are as defined above in section (I), and X is a halide ion.

The identity of the acyl halide can and will vary. As detailed above in section (I), in specific embodiments, $R^2$ may be unsubstituted or substituted $C_4$ to $C_{24}$ alkyl or $C_4$ to $C_{24}$ alkenyl. Alkyl or alkenyl groups may be linear, branched, or cyclic, and alkenyl groups may contain from one to six carbon-carbon double bonds. In some embodiments, $R^2$ may be $C_4$ to $C_{16}$ alkyl or $C_4$ to $C_{16}$ alkenyl. In other embodiments, $R^2$ may be $C_5$, $C_7$, $C_9$, $C_{11}$, $C_{13}$, or $C_{16}$ alkyl or alkenyl. Moreover, the halide X may be chloride, bromide, fluoride, or iodide. The acyl halide may be derived from a natural fatty acid (the natural fatty acid may be linear, branched, saturated, or unsaturated). Non-limiting examples of suitable acyl halides include pentanoyl halide, hexanoyl halide, ethyl hexanoyl halide, heptanoyl halide, octanoyl halide, nonanoyl halide, decanoyl halide, undecanoyl halide, dodecanoyl (lauroyl) halide, tridecanoyl halide, tetradecanoyl (myristoyl) halide, pentadecanoyl halide, hexadecanoyl (palmitoyl) halide, myristoloyl halide, palmitoloyl halide, and sapienoyl halide.

The amount of acyl halide that is contacted with the compounds of Formula (II) can and will vary. In general, the mole-to-mole ratio of the compounds having Formula (II) to the acyl halide, $R^2C(O)X$, may range from about 1:0.2 to about 1:2. In some embodiments, the mole-to-mole ratio of the compounds having Formula (II) to the acyl halide may range from about 1:0.2 to about 1:0.5, from about 1:0.5 to about 1:1, from about 1:1 to about 1:1.5, or from about 1:1.5 to about 1:2. In a specific embodiment, the mole-to-mole ratio of the compounds having Formula (II) to the acyl halide may be about 1:0.5. In another specific embodiment, the mole-to-mole ratio of the compounds having Formula (II) to the acyl halide may be about 1:1.

Contact between the compounds of Formula (II) and the acyl halide may be conducted in the presence of a catalyst and a proton acceptor. In specific embodiments, the catalyst is a nucleophilic catalyst. Non-limiting examples of suitable nucleophilic catalysts include 4-dimethylaminopyridine (DMAP), pyridine or derivatives thereof, imidazole or derivatives thereof, amidines, isothioureas, and guanidines. In a specific embodiment, the nucleophilic catalyst may be DMAP. Typically, a catalytic amount of the catalyst is used in the process.

Suitable proton acceptors include, without limit, organic bases such as triethylamine, diisopropylethylamine, N-methylmorpholine, and mixtures thereof; organic buffers (for example, 4-(2-hydroxyethyl)piperazine-1-ethanesulfonic acid (HEPES), 2 (4 morpholinyl) ethanesulfonic acid (MES), 4-morpholinepropanesulfonic acid (MOPS), 1,4-piperazinediethanesulfonic acid (PIPES), salts and/or mixtures thereof); borate salts; di- and tri-basic phosphate salts; bicarbonate salts; hydroxide salts; carbonate salts, or mixtures thereof. In general, the mole-to-mole ratio of the compounds of Formula (II) to the proton acceptor ranges from about 1:0.1 to about 1:10. In various embodiments, the mole-to-mole ratio of the compounds of Formula (II) to the proton acceptor may range from range from about 1:0.5 to about 1:5, from about 1:1 to about 1:4, or from about 1:1.8 to about 1:2.2.

The reaction may be conducted in the presence of a solvent. The solvent may be a nonpolar solvent, a protic polar solvent, an aprotic polar solvent, or a combination thereof. Non-limiting examples of suitable nonpolar solvents include benzene, butyl acetate, tert-butyl methyl ether, chlorobenzene, chloroform, chloromethane, cyclohexane, dichloromethane (DCM), dichloroethane, di-tert-butyl ether, dimethyl ether, diethylene glycol, diethyl ether, diglyme, diisopropyl ether, ethyl tert-butyl ether, ethylene oxide, fluorobenzene, heptane, hexane, methyl tert-butyl ether, toluene, and combinations thereof. Suitable protic polar solvents include without limit amides such as formamide, acetamide, and the like. Non-limiting examples of suitable aprotic polar solvents include acetone, acetonitrile, diethoxymethane, N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl) ether, N,N-dimethylacetamide (DMAC), N-methyl-2-pyrrolidinone (NMP), 1,4-dioxane, ethyl acetate, ethyl formate, formamide, hexachloroacetone, hexamethylphosphoramide, methyl acetate, N-methylacetamide, methylethyl ketone, methylisobutyl ketone, N-methylformamide, methylene chloride, methoxyethane, morpholine, nitrobenzene, nitromethane, propionitrile, propyl acetates, sulfolane, tetramethylurea, tetrahydrofuran (THF), 2-methyl tetrahydrofuran, tetrahydropyran, trichloromethane, and combinations thereof. In specific embodiments, the solvent may be dichloromethane (DCM).

The volume-to-mass ratio (mL to g) of the solvent to the compounds of Formula (II) can and will vary. Typically, the volume-to-mass ratio of the solvent to the compounds of Formula (II) may range from about 1:1 to about 100:1. In various embodiments, the volume-to-mass ratio of the solvent to the compounds of Formula (II) may range from about 1:1 to about 3:1, from about 3:1 to about 10:1, from about 10:1 to about 30:1, or from about 30:1 to about 100:1. In preferred embodiments, the volume-to-mass ratio of the solvent to the compounds of Formula (I) may range from about 10:1 to about 30:1.

The reaction may be conducted at a temperature that ranges from about −10° C. to about 50° C. In certain embodiments, the temperature of the reaction may range from about 0° C. to about 10° C., from about 10° C. to about 20° C., from about 20° C. to about 30° C., from about 30° C. to about 40° C., or greater than about 40° C. In specific embodiments, the reaction may be initiated at about 0° C. and then the temperature may be increased to about room temperature. In general, the reaction will be conducted at atmospheric pressure.

The duration of the reaction can and will vary. In general, the reaction may be allowed to proceed from about 1 hour to about 24 hours or more. In some embodiments, the reaction may be allowed to proceed overnight (or from about 12 to about 18 hours). Typically, however, the reaction is allowed to proceed for a sufficient period of time until the reaction has proceeded to the desired degree of completion, as determined by means well known to those of skill in the art. In embodiments in which the reaction is allowed to go to completion, a "completed reaction" generally means that the final reaction mixture contains a significantly diminished amount of the compound comprising Formula (II) and a significantly increased amount of the ester compound comprising Formula (Ia) compared to the amounts of each present at the beginning of the reaction.

The compounds comprising Formula (Ia) may be isolated from the reactants in the reaction mixture by means known in the art. Suitable means include extracting, washing, precipitating, filtering, distilling, evaporating, drying, chromatography, and combinations thereof. In some embodiments, individual monomers, dimers, etc. may be isolated. For example, compounds in which k varies can be separated via column chromatography.

The yield of the compounds of Formula (Ia) can and will vary. In general, the yield of the compound may be at least about 20%, at least about 30%, at least about 40%, at least about 50%, at least about 60%, at least about 70%, at least about 80%, or at least about 90%.

(b) Preparation of Compounds of Formula (Ib)

The process comprises contacting the compounds of Formula (Ia) with a salt, MA, to form the compounds of Formula (Ib) according to the following reaction scheme:

wherein $R^1$, $R^2$, Z, M, k, and n are as defined above in section (I), and A is an anion.

The salt comprises a cation, M, as described above in section (I), and an anion A. Suitable anions include, without limit, hydroxide, hydride, acetate, amide, carbonate, hydrogen carbonate, bromide, bromate, chloride, chlorate, chlorite, hypochlorite, chromate, dichromate, formate, nitrate, nitride, nitrite, perchlorate, peroxide, phosphate, hydrogen phosphate, dihydrogen phosphate, permanganate, oxide, oxalate, sulfate, sulfite, hydrogen sulfate, sulfide, thiosulfate, and thiocyanate. In some embodiments, the salt is free (e.g., is in solution). In other embodiments, the salt is bound to a resin (e.g., an ion exchange resin). In specific embodiments, the salt may be sodium hydroxide, potassium hydroxide, sodium bicarbonate, potassium bicarbonate, and the like.

The amount of salt contacted with the compounds of Formula (Ia) can and will vary. In general, the mole-to-mole ratio of the compounds of Formula (Ia) to the salt may range from about 1:0.5 to about 1:2. In specific embodiments, the mole-to-mole ratio of the compounds of Formula (Ia) to the salt may be about 1:1.

The reaction may be performed in the presence of a solvent. Suitable solvents and ratios are detailed above in section (IV)(a)(i). The reaction may proceed under homogenous or heterogeneous reaction conditions. The temperature of the reaction may vary, but generally ranges from about 15° C. to about 35° C. The duration of the reaction may vary, but generally ranges from about one hour to about one day. In general, the reaction is allowed to proceed until the reaction is complete or substantially complete, as determined by means well known to those of skill in the art.

The compounds comprising Formula (Ib) may be isolated from the reactants in the reaction mixture by means known in the art. Suitable means include extracting, washing, precipitating, filtering, distilling, evaporating, drying, chromatography, and combinations thereof.

The yield of the compounds of Formula (Ib) can and will vary. In general, the yield of the compound may be at least about 20%, at least about 30%, at least about 40%, at least about 50%, at least about 60%, at least about 70%, at least about 80%, or at least about 90%.

Definitions

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The term "acyl," as used herein alone or as part of another group, denotes the moiety formed by removal of the hydroxyl group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes saturated hydrocarbyl groups that contain from 1 to 30 carbon atoms. They may be linear, branched, or cyclic, may be substituted as defined below, and include methyl, ethyl, propyl, isopropyl, butyl, hexyl, heptyl, octyl, nonyl, and the like.

The term "alkenyl" as used herein describes hydrocarbyl groups which contain at least one carbon-carbon double bond and contain from 1 to 30 carbon atoms. They may be linear, branched, or cyclic, may be substituted as defined below, and include ethenyl, propenyl, isopropenyl, butenyl, isobutenyl, hexenyl, and the like.

The term "alkoxide" or "alkoxy" as used herein is the conjugate base of an alcohol. The alcohol may be straight chain, branched, cyclic, and includes aryloxy compounds.

The term "alkynyl" as used herein describes hydrocarbyl groups which contain at least one carbon-carbon triple bond and contain from 1 to 30 carbon atoms. They may be linear or branched, may be substituted as defined below, and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The term "aryl" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like.

Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. They may be straight, branched, or cyclic. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

Having described the invention in detail, it will be apparent that modifications and variations are possible without departing from the scope of the invention defined in the appended claims.

EXAMPLES

The following examples illustrate various embodiments of the present disclosure.

Example 1: Synthesis of Compounds

A series of ester analogs of 2-hydroxy-4-(methylthio) butanoic acid (HMTBA) (HMTBA esters, HE) comprising different length acyl groups was prepared essentially as described below for the $C_{14}$ analog.

To 2-hydroxy-4-(methylthio)butanoic acid (2.5 g) was added myristoyl chloride (3.7 mL). The reaction was heated to 65° C. for 16-18 hours and then cooled to room temperature. The crude reaction material was purified by column chromatography eluting with 100% heptanes (+1% AcOH) for 3 column volumes (CV) then via gradient to 60% ethyl acetate (+1% AcOH)/40% heptane (+1% AcOH) over 18 CV. The desired fractions were combined and concentrated to an oily residue. To the residue was added 50 mL of heptane and the heptane was removed by rotary evaporator. This was done 2× to azeotrope residual AcOH. The final residue was dried to give 2.6 g of a white solid. The name, structure, and composition by HPLC of each are presented in Table 1.

TABLE 1

| HMTBA Esters (HE) | | |
|---|---|---|
| Name | Structure | HE Composition (relative % by HPLC AUC) |
| $C_{14}$-HE (myristoyl-HE) | [structure image] | 80.5% monomer (k = 1)<br>19.5% dimer (k = 2) |
| $C_{12}$-HE (lauroyl-HE) | [structure image] | 66.5% monomer (k = 1)<br>34.5% dimer (k = 2) |

TABLE 1-continued

HMTBA Esters (HE)

| Name | Structure | HE Composition (relative % by HPLC AUC) |
|---|---|---|
| $C_{10}$-HE (caproyl-HE) | | 80.5% monomer (k = 1)<br>19.5% dimer (k = 2) |
| $C_8$-HE (octanoyl-HE) | | 68.4% monomer (k = 1)<br>25.6% dimer (k = 2)<br>5.3% trimer (k = 3)<br>0.7% tetramer (k = 4) |
| $C_6$-HE (hexanoyl-HE) | | 75.1% monomer (k = 1)<br>21.7% dimer (k = 2)<br>3.2% trimer (k = 3) |

Each acid was converted to the sodium salt (HE-Na salt) by contact with sodium bicarbonate in the presence of methanol using standard procedures.

Example 2: Determine Minimum Inhibitory Concentration (MIC) of HE-Na Salts

An initial experiment was performed in microtiter plates to determine the MIC value for the HE-Na salts over a HE-Na salt range of 1.0% (w/v) to 0.008% (w/v).

A liquid culture of *Clostridium perfringens* (ATCC 10543) was grown under anaerobic conditions in a screw-capped polypropylene centrifuge tube containing 10 mL of Reinforced Clostridial Medium (RCM; Difco Laboratories). The tube was placed into a pouch equipped with a GasPak™ EZ Anaerobic Gas Generating Sachet (Becton, Dickinson & Co.), sealed to keep oxygen levels at a minimum and incubated at 37° C. for 24 hours. Working solutions (2.0% w/v) of the HE-Na salts in sterile DI water were prepared. Water was sterilized by filtration using 0.2 μm cellulose acetate filters (Corning) and the bacterial growth medium was sterilized by autoclaving at 121° C. for 15 minutes. Sterile DI water (100 microliters) was added to each well of a 96-well microtiter plate. Next, 100 microliters of each HE-Na Salt solution was added to duplicate wells in the top row of the microtiter plate and serial two-fold dilutions were prepared by transferring 100 microliters from a well to the following well in the same column. For the last row in each column, 100 microliters was removed and discarded.

Next, a bacterial working stock was prepared by combining 2× RCM medium containing 0.3% agar (Sigma-Aldrich) with an overnight culture of *Clostridium perfringens* to achieve a bacterial concentration of approximately $1\times10^5$ CFU/ml. A 100 microliter aliquot of the bacterial working stock was added to all wells so that the final population was equal to approximately $1\times10^4$ CFU/well and the medium was diluted two fold. The 96-well plate was placed into a pouch along with a GasPak™ EZ Anaerobic Gas Generating Sachet and a moistened paper towel (to reduce evaporation) and incubated at 37° C. for 24 hours. The growth of the test organism was determined at 630 nm using a plate reader (BioTek microplate reader) and MIC values were determined.

Table 2 shows the MIC values for the various HE-Na salts tested for *C. perfringens* in RCM with 0.15% agar. The number in parentheses is the number of experimental repeats. The minimum inhibitory concentration (MIC) is defined as the lowest concentration of test compound that prevented bacterial growth.

TABLE 2

| MIC Values<br>MIC Values of HEs against *Clostridium perfringens* | |
|---|---|
| HE-Na Salt | MIC values (% w/v) |
| $C_6$ HE Na | >1.0 (3X) |
| $C_8$ HE-Na | 0.063 (3X) |
| $C_{10}$ HE-Na | 0.016 (3X) |
| $C_{12}$ HE-Na | <0.008 (3X) |
| $C_{14}$ HE-Na | <0.008 (3X) |

The MIC values for the $C_{12}$ and $C_{14}$ HE-Na salts were determined to be lower than the lowest test concentration in the above experiment.

Example 3: Paper Disc Diffusion Assay

The antimicrobial activity of each of $C_{12}$ HE and $C_{14}$ HE was determined using paper disk diffusion method against three known bacterial strains with gut health significance. Selective media agar plate for each bacterial strain was prepared as given below.

| Strain | Selective media (Agar plates) | Overlay (soft agar) |
| --- | --- | --- |
| Lactobacillus casei | de Man, Rogosa and Sharpe (MRS) | MRS |
| Clostridium perfringens | Tryptic soy agar (TSA) with thioglycolate | TSA with thioglycolate |
| Enterococcus cecorum | Blood agar | Brain heart infusion |

The solidified agar plates were overlaid with soft agar (50° C.) after inoculating with each of the strains (~100 µL of culture with $10^8$ cfu/mL). Plates were allowed to solidify at room temperature. Approximately 8-mm paper disks were soaked with 20 µL of sterile buffer (Control) or different concentrations (i.e., 1, 0.5, 0.25, 0.125, 0.0625, 0.03125, 0.015, 0.008% w/v in sterile buffer) of each product and placed on the solidified plates. All plates were incubated at 37° C. for 24 h, and inhibition zones were measured. Test was replicated two times for each product per organism.

Antimicrobial activity index (I) was used to compare the activity of the products, where I ($mm^3/µg$) is the Volume ($mm^3$) of zone of inhibition/µg of the product. Higher the value of I, the more potent is the product. I is calculated using the following formula:

$$I = \frac{V}{MIC}$$

$$V = \frac{2}{3}\pi r^3,$$

wherein r is the radius of zone of inhibition at minimum inhibitory concentration (MIC).

Figure 1:
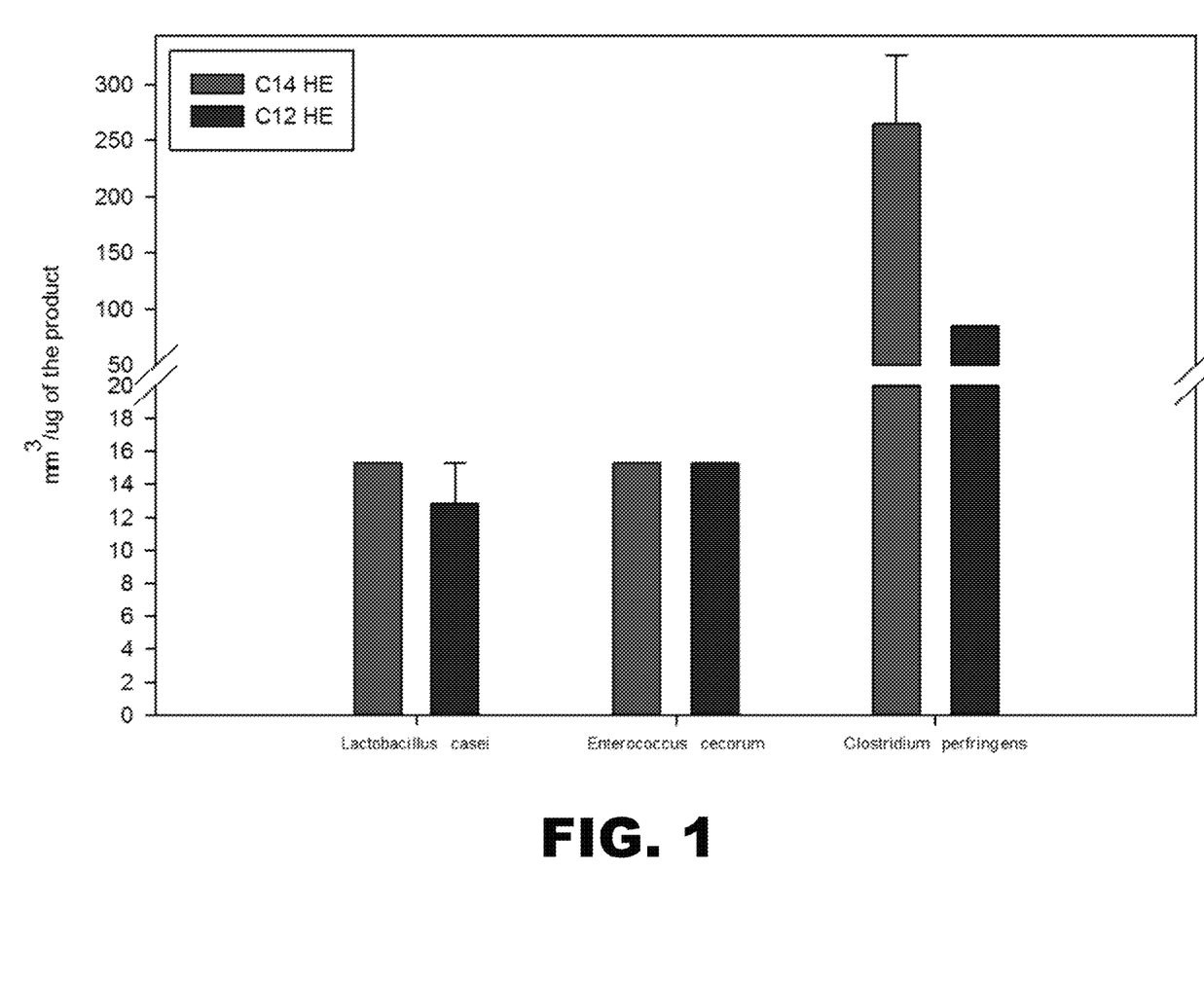
FIG. 1 illustrates the antimicrobial activity index (I) of two HMTBA esters against the indicated bacteria. (I=mm$^3$/μg of HMTBA ester.)

Results from the paper disc diffusion assay showed that $C_{14}$ HE had better antimicrobial activity against *C. perfringens* compared to $C_{12}$ HE (FIG. 1).

Example 4: In Vitro Nutrient Media (TSA-Thioglycolate) Assay

For this assay, sterile tubes of TSA-thioglycolate broth were inoculated with 250 µL of either $C_{12}$ HE or $C_{14}$ HE (2% w/v) and *C. perfringens* culture (~100 µL of culture with $10^8$ cfu/mL). A positive control was set up using Bacitracin, which is an antibiotic used against necrotic enteritis (caused by *C. perfringens*), both therapeutically as well as prophylactically. The tubes were incubated overnight under anaerobic conditions and the *C. perfringens* counts (cfu/mL) were determined.

Results showed complete inhibition of *C. perfringens* growth by $C_{14}$ HE and $C_{12}$ HE, an effect similar to that of Bacitracin.

Example 5: Crop, Pro Ventricular, and Ileal In Vitro Assay

In vitro assays were conducted that simulate the conditions of the crop, proventriculus, and ileum of the avian digestive system. Supernatant from feed digesta for crop, proventriculus, and ileum were obtained according to the procedure described by Annett el al., 2002 (Avian Pathology 2002, 31: 599-602). About 3 mL of supernatant was mixed with 6 mL of sterile TSA-thioglycolate and 100 µL of *C. perfringens* culture ($10^8$ cfu/mL) as well as 250 µL of 2% w/v solution of $C_{12}$ HE or $C_{14}$ HE. (Bacitracin was used a positive control.) After incubating the mixture for 24 h, samples were collected from each tube, serial dilutions were made in sterile normal saline, and plated on TSA with thioglycolate to measure the CFUs. Three replicates were run for each product for each assay.

Figure 2:
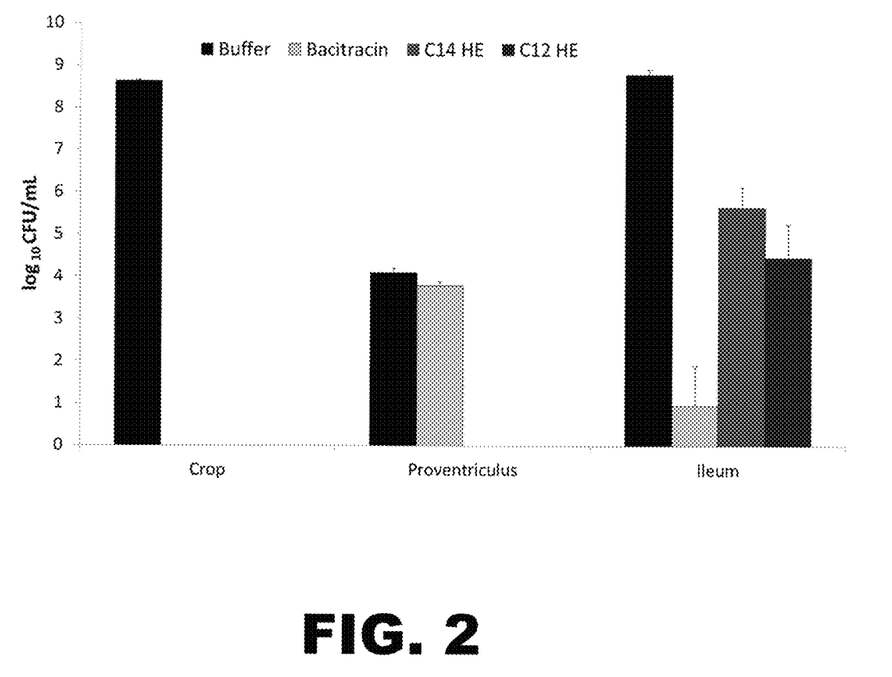
FIG. 2 presents Clostridial counts obtained after treatment with the indicated compounds in crop, proventricular, or ileal in vitro assays.

The results are presented in FIG. 2. In the crop assay, $C_{14}$ HE, $C_{12}$ HE, and Bacitracin showed complete inhibition of the growth of *C. perfringens*. $C_{14}$ HE and $C_{12}$ HE were effective against *C. perfringens* in the proventricular assay, while Bacitracin was not effective (counts were similar to that of the buffer). In the ileal assay, $C_{14}$ HE and $C_{12}$ HE did not result in a complete reduction (~4 $\log_{10}$ reduction) of *C. perfringens*, while Bacitracin resulted in almost complete reduction. In this assay, the pH values of the crop, proventricular, and ileal assay supernatants were 5.34, 2.54, and 7.01, respectively.

What is claimed is:

1. An antimicrobial composition comprising at least one compound of Formula (I) and at least one agent chosen from an essential oil, a metal chelate, a mineral, an amino acid, an organic acid, a vitamin, an antioxidant, a polyunsaturated fatty acid, a prebiotic, a probiotic, a symbiotic, an enzyme, an ionophore, a mycotoxin binder, an antiparasitic agent, an antibiotic, a herbal extract, a pigment, or combination thereof, the compound of Formula (I) having the following structure:

wherein:
 $R^1$ is hydrocarbyl or substituted hydrocarbyl;
 $R^2$ is hydrocarbyl or substituted hydrocarbyl;
 Y is hydrogen, ammonium, an alkali metal, an alkaline earth metal, or a transition metal;
 Z is sulfur or selenium;
 k is an integer of 1 or greater; and
 n is an integer of 1 or greater;
 provided that when k is 1, Z is sulfur.

2. The antimicrobial composition of claim 1, wherein $R^1$ is alkyl, substituted alkyl, alkenyl, substituted alkenyl, aryl or substituted aryl, and $R^2$ is alkyl, substituted alkyl, alkenyl, substituted alkenyl, aryl, or substituted aryl.

3. The antimicrobial composition of claim 2, wherein $R^1$ is $C_1$-$C_6$ alkyl, and $R^2$ is $C_4$-$C_{24}$ alkyl or $C_4$-$C_{24}$ alkenyl, k is from 1 to 10, and n is from 1 to 3.

4. The antimicrobial composition of claim 3, wherein $R^1$ is methyl, $R^2$ is $C_4$-$C_{16}$ alkyl, Y is hydrogen or an alkali metal, Z is sulfur, and n is 2.

5. The antimicrobial composition of claim 1, wherein
the essential oil is chosen from cinnamon, lavender, oregano, rosemary, or thyme;
the metal chelate is an amino acid chelate or an organic acid chelate of calcium, chromium, copper, iron, magnesium, manganese, selenium, or zinc;
the mineral is a salt, chelate, or complex of calcium, chromium, copper, iodine, iron, magnesium, manganese, molybdenum, phosphorus, potassium, selenium, or zinc;
the enzyme is chosen from phytases, proteases, or carbohydrases;
the ionophore is chosen from bambermycin, decoquiate, declazuril, lasalocid, maduramicin, monensin, narasin, nicarazin, nystatin, robenedine, salinomycin, or semduramicin;
the mycotoxin binder is chosen from charcoal, activated carbon, phyllosilicates, tectosilicates, aluminosilicates, bentonites, zeolites, clinoptilolites, montmorillonites, cellulose, glucomannans, peptidoglycans, cholestyramine, polyvinylpyrrolidone, yeast cell wall extracts, or bacterial extracts, and
the antibiotic is chosen from bacitracin, carbadox, ceftiofur, enrofloxacin, florfenicol, laidlomycin, linomycin, oxytetracycline, roxarsone, tilmicosin, tylosin, or virginiamycin.

6. The antimicrobial composition of claim 1, wherein the composition is part of a feed supplement, feed premix, feed blend, pet food, pet treat, or packaging material.

7. A feed composition comprising at least one compound of Formula (I) and at least one nutritive agent, the compound of Formula (I) having the following structure:

wherein:
R$^1$ is hydrocarbyl or substituted hydrocarbyl;
R$^2$ is hydrocarbyl or substituted hydrocarbyl;
Y is hydrogen, ammonium, an alkali metal, an alkaline earth metal, or a transition metal;
Z is sulfur or selenium;
k is an integer of 1 or greater; and
n is an integer of 1 or greater;
provided that when k is 1, Z is sulfur.

8. The feed composition of claim 7, wherein R$^1$ is alkyl, substituted alkyl, alkenyl, substituted alkenyl, aryl or substituted aryl, and R$^2$ is alkyl, substituted alkyl, alkenyl, substituted alkenyl, aryl, or substituted aryl.

9. The feed composition of claim 8, wherein R$^1$ is $C_1$-$C_6$ alkyl, and R$^2$ is $C_4$-$C_{24}$ alkyl or $C_4$-$C_{24}$ alkenyl, k is from 1 to 10, and n is from 1 to 3.

10. The feed composition of claim 9, wherein R$^1$ is methyl, R$^2$ is $C_4$-$C_{16}$ alkyl, Y is hydrogen or an alkali metal, Z is sulfur, and n is 2.

11. The feed composition of claim 7, wherein the nutritive agent is chosen from a carbohydrate source, a fat source, a protein source, an amino acid, an alpha hydroxy acid, or combination thereof.

12. The feed composition of claim 7, further comprising at least one agent chosen from an essential oil, a metal chelate, a mineral, an amino acid, an organic acid, a vitamin, an antioxidant, a polyunsaturated fatty acid, a prebiotic, a probiotic, a symbiotic, an enzyme, an ionophore, a mycotoxin binder, an antiparasitic agent, an antibiotic, a herbal extract, a pigment, a filler, a diluent, a binder, a pH modifier, an anti-caking agent, a disintegrant, a lubricant, a dispersant, a preservative, a flavoring agent, a sweetening agent, a taste masking agent, a coloring agent, or combination thereof.

13. The feed composition of claim 7, wherein the feed composition is part of a feed premix, grain mix, feed blend, pet food, or pet treat.

14. A method for inhibiting the growth of at least one microbe, the method comprising contacting the microbe with an effective amount of at least one compound of Formula (I):

wherein:
R$^1$ is hydrocarbyl or substituted hydrocarbyl;
R$^2$ is hydrocarbyl or substituted hydrocarbyl;
Y is hydrogen, ammonium, an alkali metal, an alkaline earth metal, or a transition metal;
Z is sulfur or selenium;
k is an integer of 1 or greater; and
n is an integer of 1 or greater.

15. The method of claim 14, wherein R$^1$ is alkyl, substituted alkyl, alkenyl, substituted alkenyl, aryl or substituted aryl, and R$^2$ is alkyl, substituted alkyl, alkenyl, substituted alkenyl, aryl or substituted aryl.

16. The method of claim 15, wherein R$^1$ is $C_1$-$C_6$ alkyl, and R$^2$ is $C_4$-$C_{24}$ alkyl or $C_4$-$C_{24}$ alkenyl, k is from 1 to 10, and n is from 1 to 3.

17. The method of claim 16, wherein R$^1$ is methyl, R$^2$ is $C_4$-$C_{16}$ alkyl, Y is hydrogen or an alkali metal, Z is sulfur, and n is 2.

18. The method of any claim 14, wherein the microbe is a gram positive bacterium.

19. The method of claim 14, wherein the microbe is within an alimentary canal organ or on a surface of a subject, the subject being human, swine, poultry, ruminant, companion animal, or aquatic organism.

20. The method of claim 19, wherein the compound of Formula (I) is administered orally to the subject as part of a composition further comprising at least one agent chosen from an essential oil, a metal chelate, a mineral, an amino acid, an organic acid, a vitamin, an antioxidant, a polyunsaturated fatty acid, a prebiotic, a probiotic, a symbiotic, an enzyme, an ionophore, a mycotoxin binder, an antiparasitic agent, an antibiotic, a herbal extract, a pigment, or combination thereof; or the compound of Formula (I) is administered orally to the subject as part of a feed composition further comprising at least one nutritive agent chosen from a carbohydrate source, a fat source, a protein source, an amino acid, an alpha hydroxy acid, or combination thereof.

21. The method of claim 19, wherein the compound of Formula (I) is applied topically to the subject as part of a composition further comprising at least one agent chosen from an essential oil, a metal chelate, a mineral, an amino acid, an organic acid, a vitamin, an antioxidant, a polyunsaturated fatty acid, a prebiotic, a probiotic, a symbiotic, an enzyme, an ionophore, a mycotoxin binder, an antiparasitic agent, an antibiotic, a herbal extract, a pigment, or combination thereof.

22. The method of claim 14, wherein the microbe is within or on a surface of an object, the object being food or feed, food or feed product, food or feed preparation equipment, food or feed packing material, health care equipment, medical devices, or packaging for household, healthcare, or industrial products.

* * * * *